United States Patent [19]

Yamada et al.

[11] Patent Number: 5,401,643
[45] Date of Patent: * Mar. 28, 1995

[54] METHOD OF PREPARING AN ACTIVE HUMAN NEUTROPHIL CHEMOTACTIC FACTOR POLYPEPTIDE

[75] Inventors: Masaaki Yamada, Kyoto; Ryuji Furuta, Ohtsu; Junichi Yamagishi, Nara, all of Japan; Kouji Matsushima, Frederick, Md.

[73] Assignees: Dainippon Pharmaceutical Co., Ltd., Osaka, Japan; The United States of America as represented by the Department of Health and Human Services, Washington, D.C.

[*] Notice: The portion of the term of this patent subsequent to Apr. 26, 2011 has been disclaimed.

[21] Appl. No.: 855,471

[22] Filed: Mar. 23, 1992

Related U.S. Application Data

[63] Continuation of Ser. No. 613,445, Nov. 13, 1990, abandoned, which is a continuation of Ser. No. 237,741, Aug. 29, 1988, abandoned.

[51] Int. Cl.⁶ .................... C12P 21/02; C12P 19/34; C12N 15/00; C12N 7/00
[52] U.S. Cl. .................... 435/69.5; 435/122.3; 435/252.33; 435/320.1; 530/412; 530/351
[58] Field of Search ............ 435/69.1, 69.5, 172.3, 435/252.33, 320.1; 530/412

[56] References Cited

U.S. PATENT DOCUMENTS

| | | | |
|---|---|---|---|
| 4,511,502 | 4/1985 | Builder et al. | 530/417 |
| 4,897,348 | 1/1990 | Johnson et al. | 435/69.1 |
| 5,026,639 | 6/1991 | Johnson et al. | 435/69.1 |

FOREIGN PATENT DOCUMENTS

WO89/04836  6/1989  WIPO.

OTHER PUBLICATIONS

Matsushima et al, Jun. 1988, pp. 1883–1893, *J. Exp. Med* vol. 167.

Peters, M. A. et al., "Expression of a Biologically Active Analog of SomatomedinC/Insulin–like Growth Factor", *Gene*, 35 pp. 83–89 1985.

Waltz et al., Biochemical and Biophysical Research Communications, vol. 149, No. 2 (1987), pp. 755–761.

Gregory et al., Biochemical and Biophysical Research Communications, vol. 151, No. 2 (1988) pp. 883–890.

Gubler et al., Jour. of Immunology, vol. 136, No. 7 (1986) pp. 2492–2497.

Mandecki, W. et al., 'Chemical Synthesis of a Gene Encoding The Human Complement Fragment C5a and its Expression in *Escherichia coli*,' *Proc. Nall. Acad. Sci.* U.S.A. vol. 82 (1985) pp. 3543–3547.

Marston F. A. O., 'The Purification of Eukaryotic Polypeptides Synthesized in *Escherichia coli*', *Biochem J.*, vol. 240, pp. 1–12, 1986.

Schmid, J. et al. 'Induction of mRNA for a Serine Protease and a β-Thromboglobulin-Like Protein in Mitogen–Stimulated Human Leukocytes', *J. Immunology*, vol 139, No. 1, pp. 250–256 (1987).

*Primary Examiner*—Garnette D. Draper
*Assistant Examiner*—Marianne Porta Allen
*Attorney, Agent, or Firm*—Birch, Stewart, Kolasch & Birch

[57] ABSTRACT

A simple and efficient method of preparing active recombinant human neutrophil chemotactic factor. The human neutrophil chemotactic factor (NCF) is solubilized from a transformant cell homogenate using urea or guanidine hydrochloride. The polypeptide is further purified from the solution using conventional protocols such as CM-Sepharose CL-6B, HW-55 column, etc.. By using this method, large amounts of active human NCF can be recovered and purified.

10 Claims, 13 Drawing Sheets

Human NGF cDNA clone: pUC 19-1.7-5
  ├─ digested with PstI and EcoRI
  ▼
PstI-EcoRI-DNA fragment
  ├─ cloned into M13mp18 vector
  ├─ infected E.Coli JM105
  ▼
Recombinant phage
  ├─ infected E. coli CJ236
  ├─ cultivated in uridine containing medium
  ▼
uracil containing DNA template
  ├─ annealed a mutagenic 33-mer primer [E]
  ▼

```
                      AATT
              T              A
               T            T
                T          G
         GTTTTGCCAAGG    AGTGCTAAAG
  ─── TCCACGTCAAAACGGTTCC - TCACGATTTC ───
```

Uracil containing DNA template

FIG. 1C

```
├─ extended the primer with T4 DNA
│   polymerase
│
├─ ligated the ends with T4 DNA
│   ligase
▼
```
Heteroduplex

```
├─ transformed E. coli JM105
▼
```
Mutated Double-Stranded DNA

```
├─ digested with DraI and EcoRI
▼
```
NGF (DraI-EcoRI) – fragment

DraI                 EcoRI              XhoI
↓                   ↓                ↓

```
        1
   MetSerAlaLys    AlaGlu     AsnSer
AAATTATGAGTGCTAAAG...GCTGAG    AATTCATGATGAC
TTTAATACTCACGATTTC...CGACTCTTAA' GTACTACTGAGCT
```

NGF (DraI-EcoRI)-fragment

|

FIG. 2A

| FIG. 2B |
|---|
| FIG. 2C |
| FIG. 2D |
| FIG. 2D |
| FIG. 2E |
| FIG. 2F |

FIG. 3A

| FIG. 3B |
|---|
| FIG. 3C |

FIG. 3B

Human IL-1α cDNA: pHL4
└─ digested with PstI
↓ cDNA insert
└─ digested with EcoRI
   and BstNI
↓

EcoRI-BstNI-fragment        Synthetic DNA
                            adaptor [H]
        ↓                         ↓
        └─ ligated with T4 DNA ligase
        ↓
                            Synthetic DNA
                            adaptor [J]
        ↓                         ↓
        └─ ligated with T4 DNA
           ligase
        ↓

METHOD OF PREPARING AN ACTIVE HUMAN NEUTROPHIL CHEMOTACTIC FACTOR POLYPEPTIDE

This application is a continuation of now abandoned application Ser. No. 07/613,445, filed Nov. 13, 1990, which is a continuation of now abandoned application Ser. No. 07/237,741, filed Aug. 29, 1988.

This invention relates to a method of preparing a human neutrophil chemotactic factor polypeptide from transformant cells harbouring an expression vector for producing the said polypeptide.

BACKGROUND OF THE INVENTION

Human neutrophil chemotactic factor(abbreviated NCF hereinafter) is a physiologically active polypeptide, which plays an important role in developmental and homeostatic mechanism, such as migration (homing) of T lymphocytes to thymus and lymphonodes, and in the modulation of immuno responses. It has been reported that NCF has biological activities to attract neutrophils and lymphocytes, and to activate these cells (Yoshimura, T. et al., *J. Immunol.*, 139, 788,1987; Walz, A. et al., *Biochem. Biophys. Res. Commun.*, 149, 755, 1987; Gregory, H. et al., *Biochem. Biophys. Res. Commun.*, 151, 833, 1988). These findings indicate that NCF is a useful immunotherapeutic agent for patients with malignant tumors and immunodeficiency diseases.

The present inventors have succeeded in the production of human NCF by recombinant DNA technology using *E. coli* as a host cell and also in the isolation of the said polypeptide from the soluble fraction of the transformanthomogenate, and a patent application on this invention was filed with the USPTO on May 2, 1988 as Ser. No. 189,164 now abandoned.

SUMMARY OF INVENTION

The inventors investigated to find a simple and efficient method for preparing the human NCF polypeptide from the transformant-homogenate. It has been unexpectedly found that a large amount of the human NCF polypeptide produced in *E. coli* cells harbouring an expression vector encoding the said polypeptide by recombinant DNA technology is mainly distributed in a precipitate fraction collected by centrifugation from the transformant-homogenate, and that the active human NCF polypeptide can be obtained efficiently from the above precipitate fraction simply by treating with a protein denaturant such as urea and guanidine hydrochloride and removing the said denaturant, for example by dialysis.

OBJECTS OF THE INVENTION

The object of this invention is to propose the method for preparing a large amount of the active human NCF polypeptide from the transformant-homogenate.

The object of this invention is also to propose the simple and efficient method for purification of the active human NCF polypeptide from the precipitate fraction of the transformant-homogenate.

Other objects will be understood from the following description.

BRIEF DESCRIPTION OF THE DRAWINGS

FIG. 1A shows the arrangement of FIGS. 1B-1D.
FIGS. 1B-1D show a process of constructing an expression plasmid pHNP101 (Referential Example 2);
FIG. 2A shows the arrangement of FIGS. 2B-2F.
FIG. 3A Shows the arrangement of FIGS. 3B-3C.
FIGS. 3B-3C show a process of constructing an expression plasmid pHIPH383a (Referential Example 4).

DESCRIPTION OF THE INVENTION

Figure 1D:
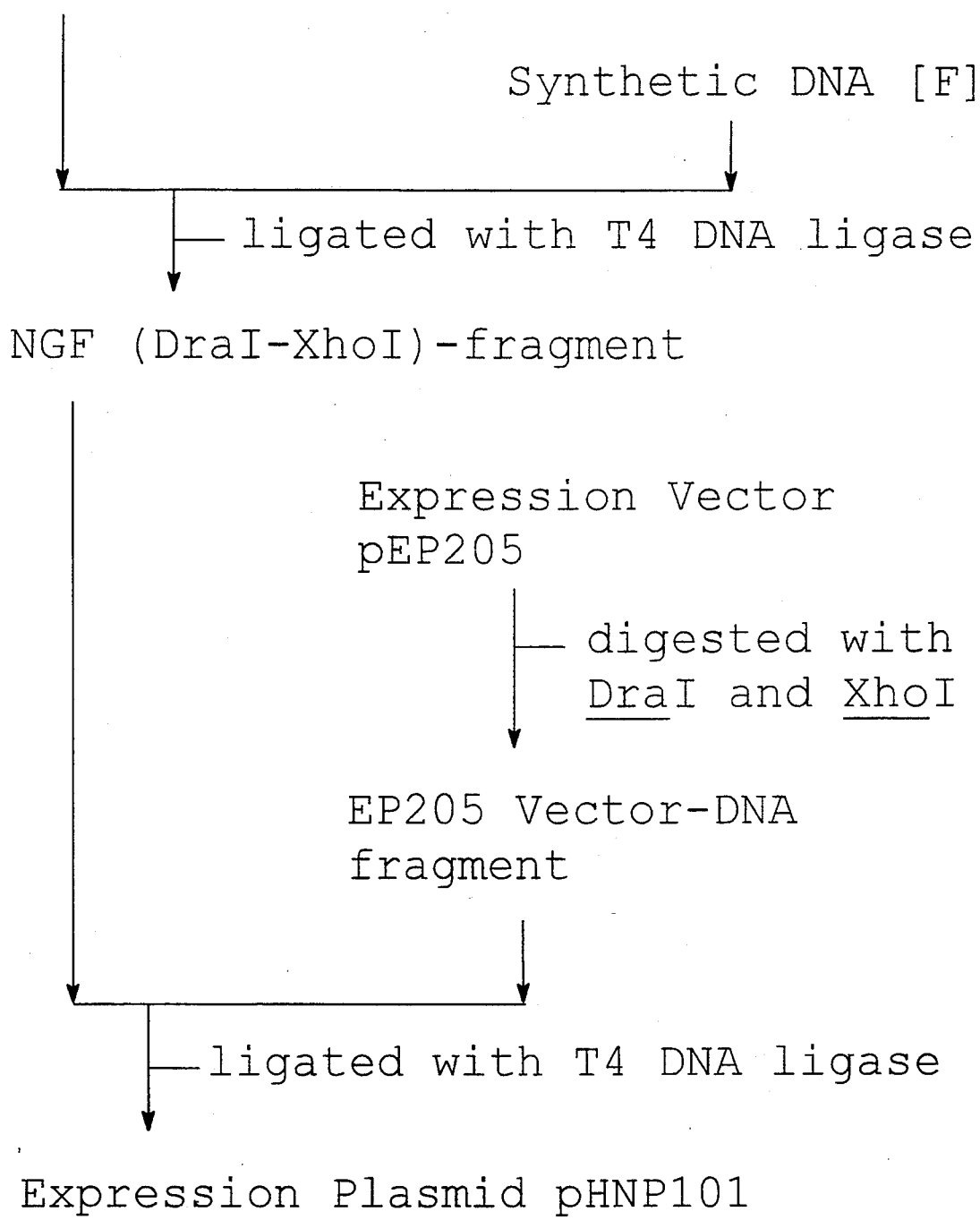
Figure 2B:
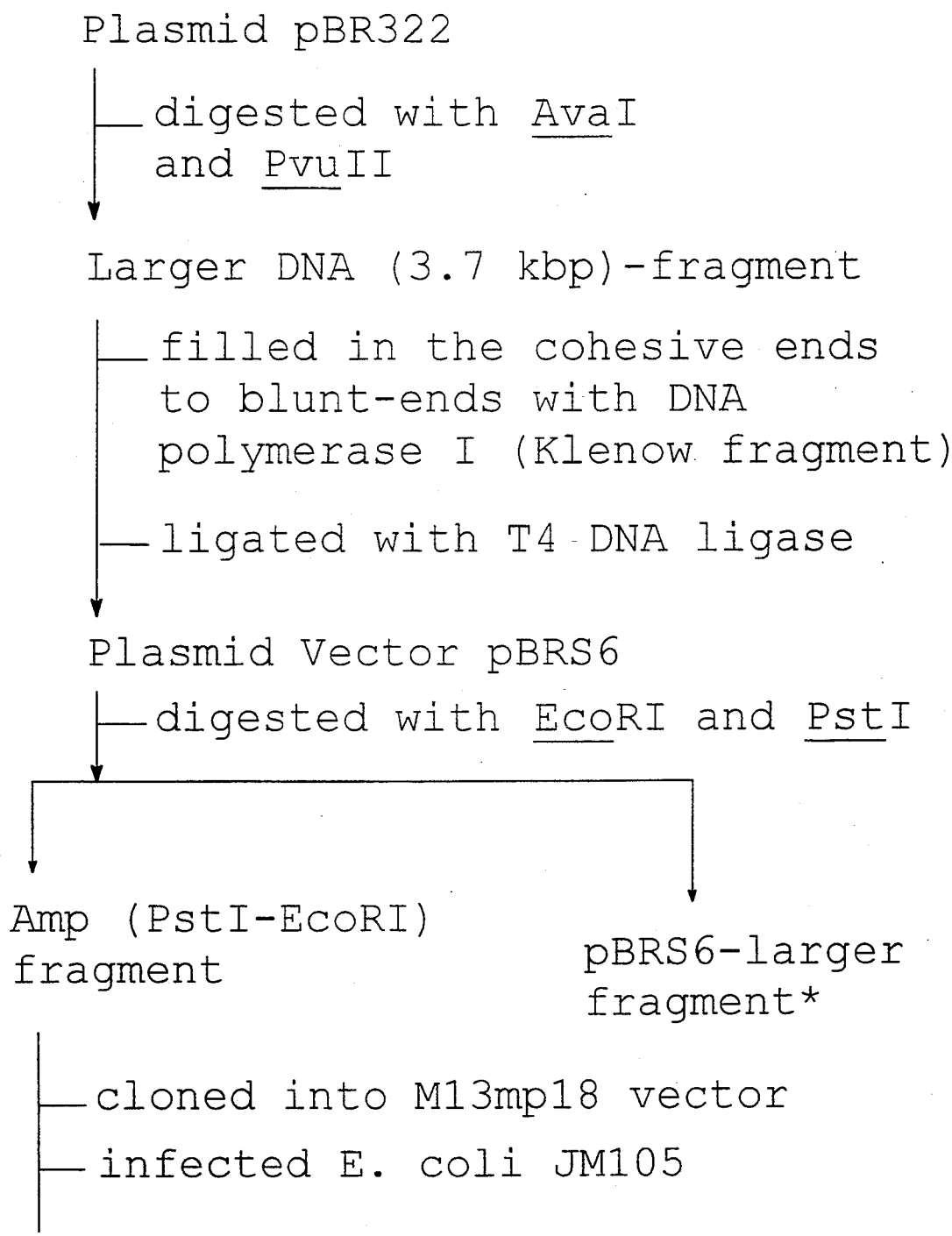
FIGS. 2B-2F show a process of constructing an expression vector pEP205 (Referential Example 3)
Figure 2C:
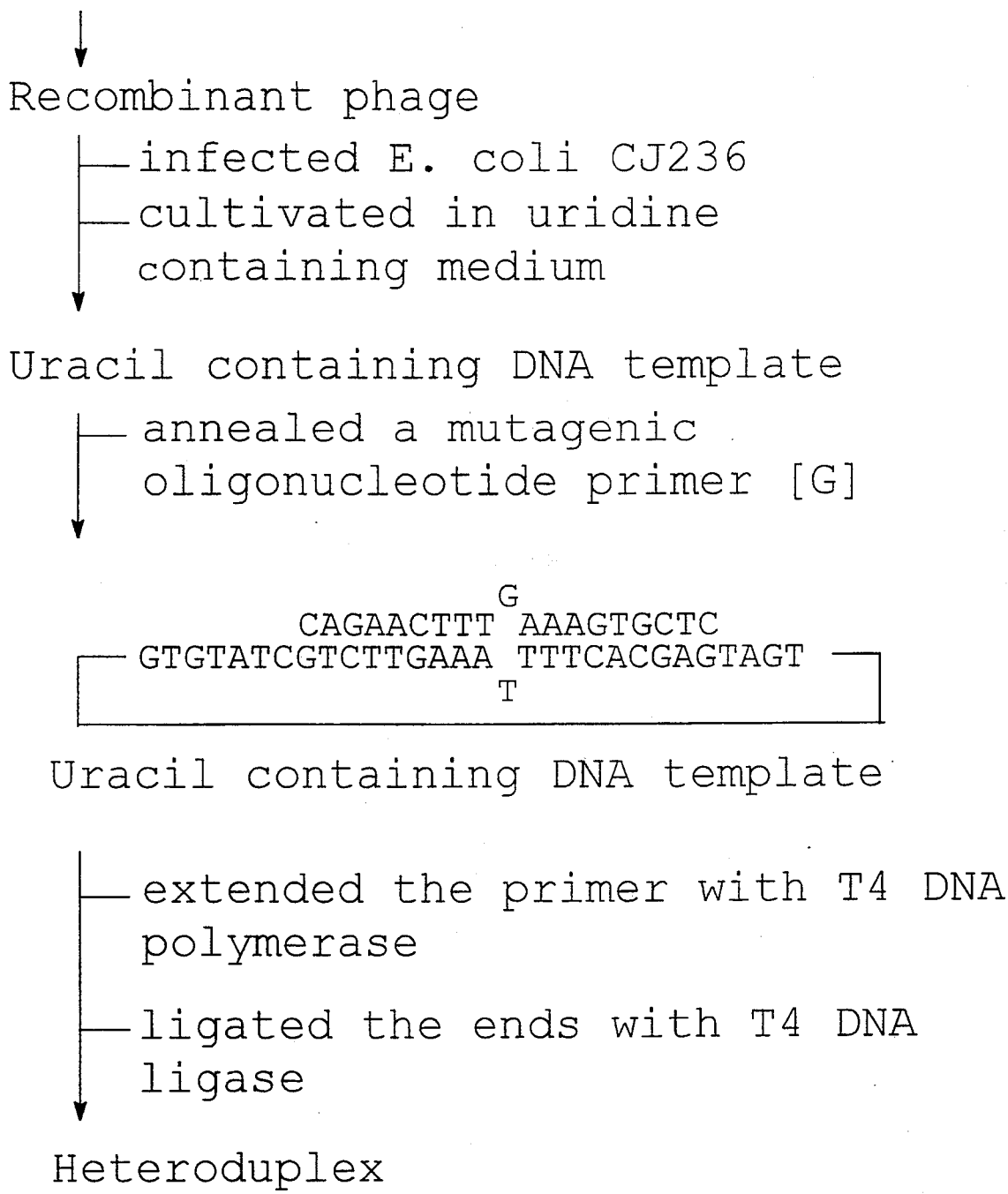
Figure 2D:
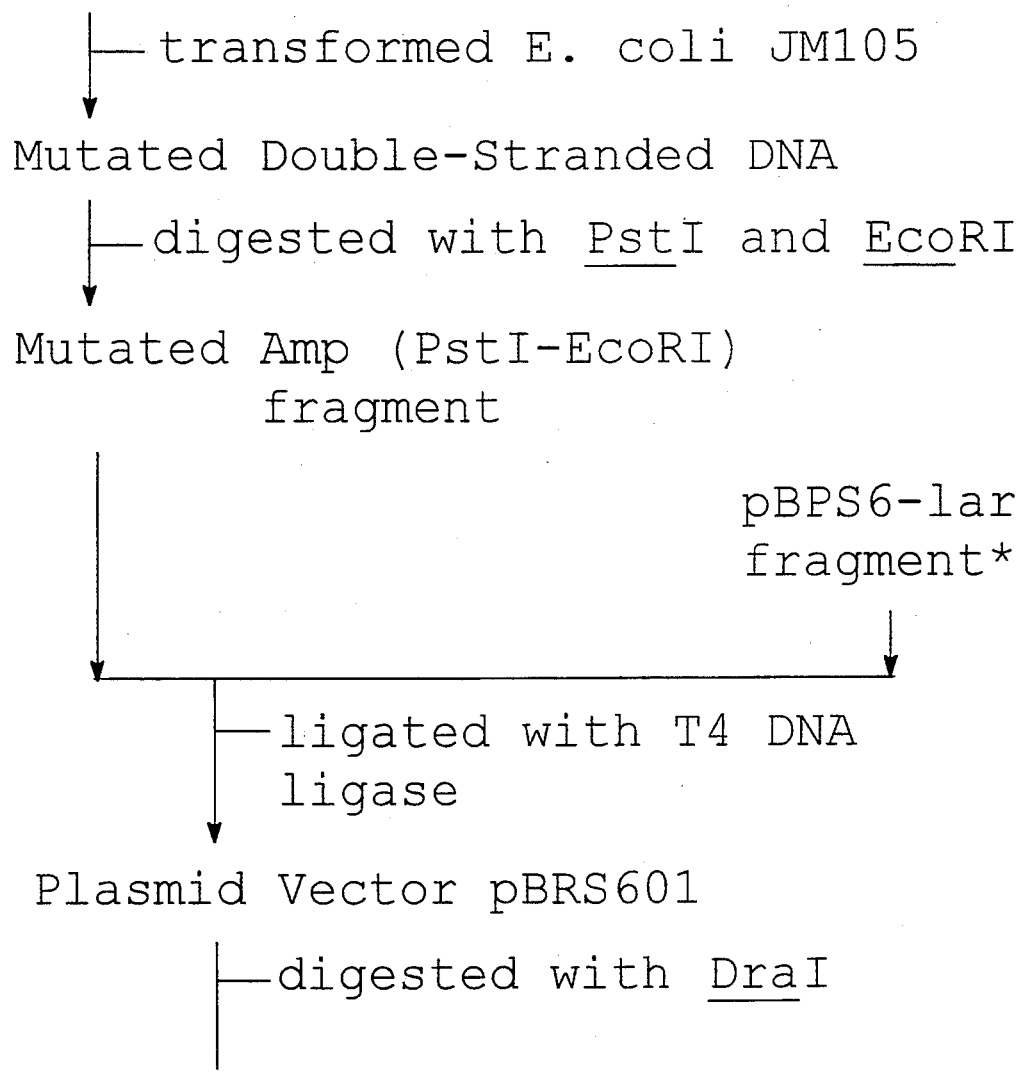
Figure 2E:
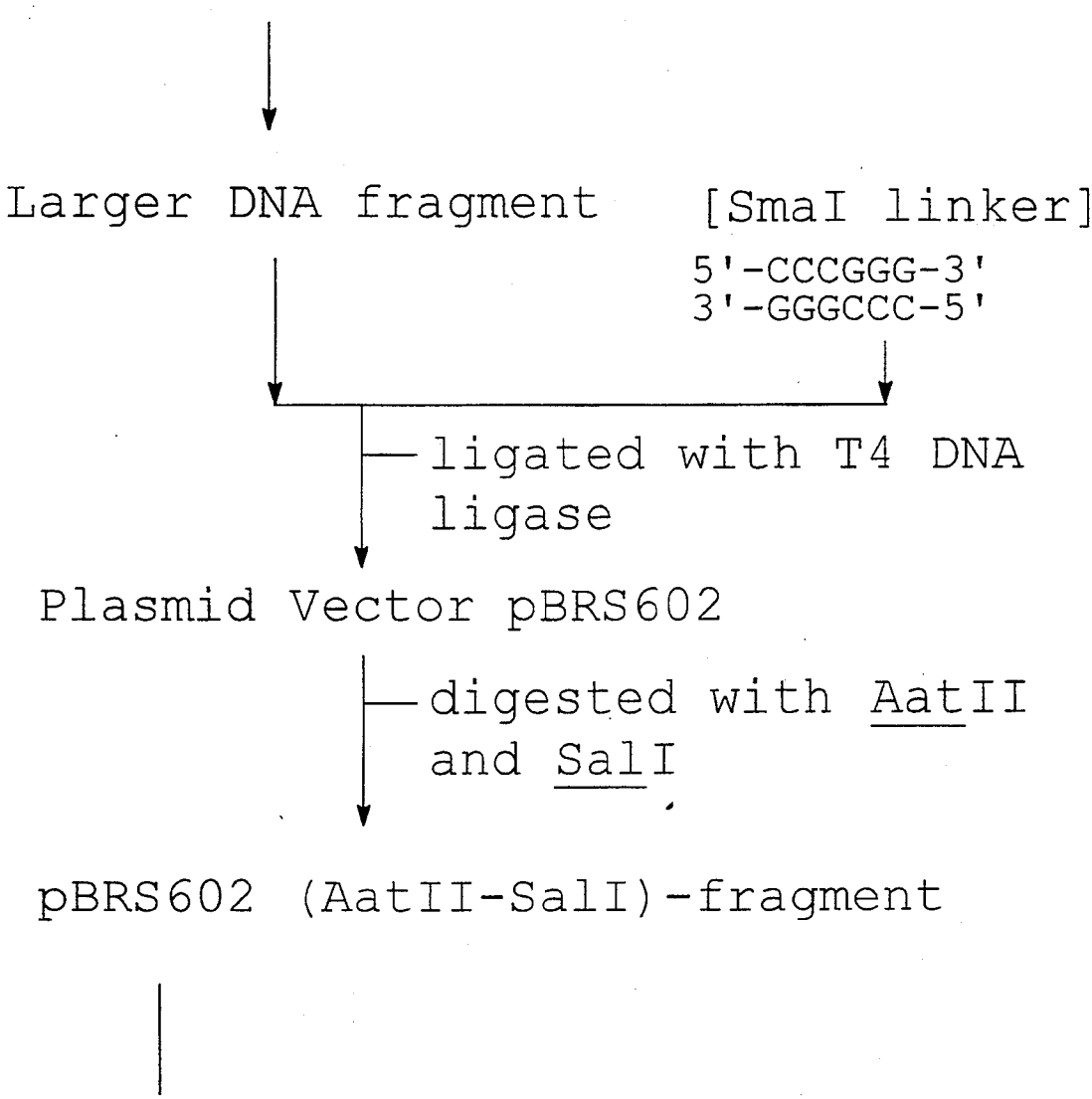
Figure 2F:
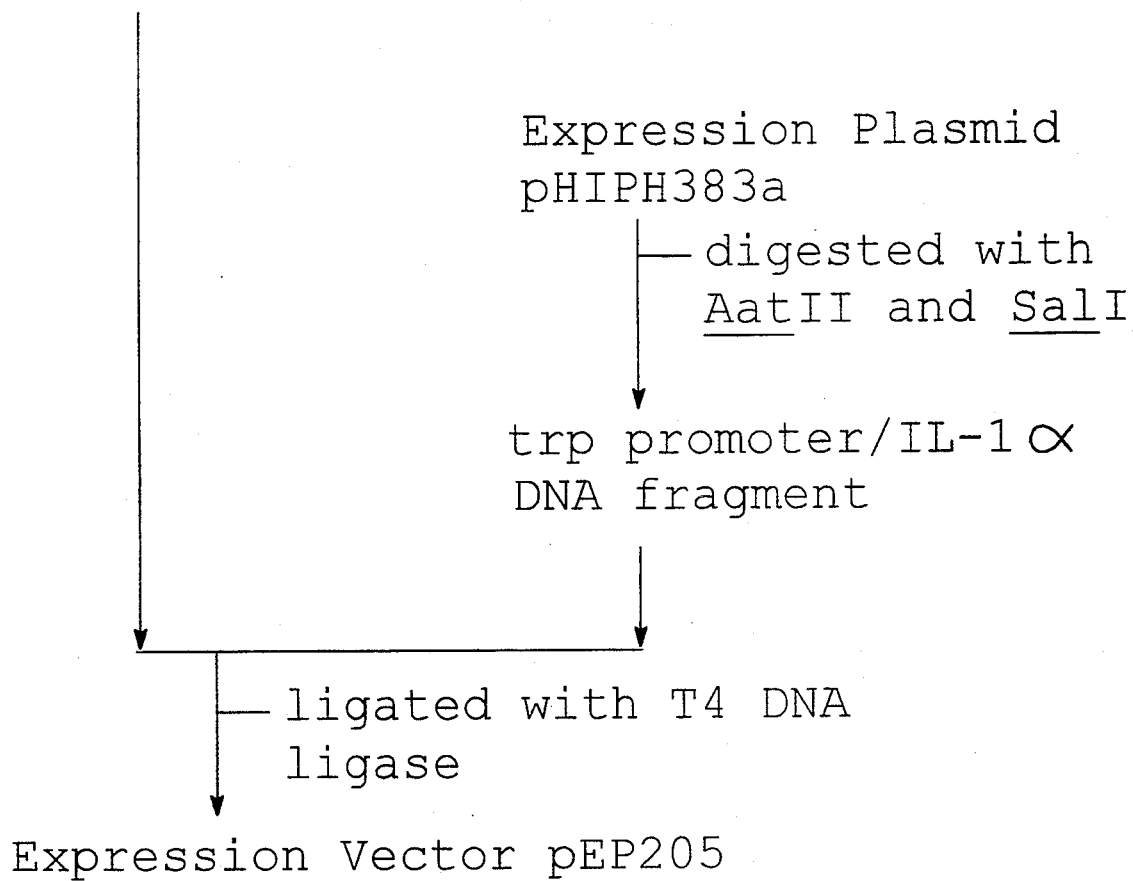

A typical amino acid sequence of the human NCF polypeptide is represented by the formula [I] shown in Table 1. However, human NCF means not only a polypeptide consisting of said amino acid sequence, but also polypeptides which have similar sequence as represented by the formula [I] shown in Table 1 and possess human NCF activity.

To describe this invention more in detail, the precipitate fraction of the transformant-homogenate is dissolved with the protein denaturant, for example urea or guanidine hydrochloride preferably at a final concentration of more than 4M, more preferably at 6 to 10M, followed by removing the said denaturant, such as by dialysis, which is carried out preferably against 10–50 mM phosphate or Tris-HCl buffer (pH 6–8). Then, only the essentially insoluble material containing the modified NCF is reprecipitated. By removing the resulting precipitate, the solution containing a large amount of the soluble active human NCF polypeptide can be easily obtained.

Prior to the separation of the precipitate fraction from the transformant-homogenate it is preferable to carry out the treatment for break-down of nucleic acids in the transformant-homegenate by digestion with deoxyribonuclease.

The soluble active NCF polypeptide recovered from the above precipitate fraction can be further purified, for example by combination of treatment for salting-out, anion and/or cation exchange chromatography, ultrafiltration, gel filtration, dialysis, electrophoresis, affinity chromatography using specific antibodies,and so on.

The human NCF polypeptide in transformant cells is produced by cultivating the cells transformed with the expression vector constructed with the DNA encoding the human NCF polypeptide. Namely, in the first place, the expression plasmid for producing the human NCF polypeptide can be constructed, for example according to Referential Example 2 with the DNA encoding the said polypeptide, which is isolated, for example according to the method as described in Referential Example 1 or by the total synthesis using conventional methods. As a second step, a transformant cell for producing the human NCF polypeptide can be obtained by introducing the above expression plasmid according to the method of Cohen et al. (*Proc. Natl. Acad. Sci.*, USA, 69, 2110, 1972). As a final step, the human NCF polypeptide can be produced by cultivating the resulting transformant cells under suitable culture conditions.

In addition the transformant-homogenate can be prepared by destroying the cells, for example by lysozyme digestion and freeze-thawing, sonication or by using a French press.

Chemical and biological properties of the human NCF prepared by Example 1 were identical with that of the human NCF polypeptide prepared from the soluble fraction of the transformant-homogenate according to the method as described in Referential Example 2, by the peptide mapping analysis performed by high-performance liquid chromatography after protease digestion of each human NCF polypeptide, and by neutrophil chemtactic assay measured in a multiwell chemotaxis Boyden chamber (Neuro Probe, Inc., USA).

For simplification of the description, the following abbreviations are used in the present specification and claims.

A: adenine
C: cytosine
G: guanine
T: thymine
I: inosine
dATP: deoxyadenosine triphosphate
dCTP: deoxycytosine triphosphate
dGTP: deoxyguanosine triphosphate
dTTP: deoxythymidine triphosphate
ATP: adenosine triphosphate
DNA: deoxyribonucleic acid
cDNA: complementary DNA
kbp: kilobase pairs
SD sequence: Shine-Dalgarno sequence
kD: kilodaltons
SDS: sodium laurylsulfate In the present specification and claims, the nucleotide sequence shown by a single strand is nucleotide sequence of a sense strand, and the left end is a 5'-terminus and the right end is a 3'-terminus. In the amino acid sequence, the left end is an N-terminus, and the right end is a C-terminus.

The following Examples and Referential Examples illustrate this invention more specifically.

It should be understood however that the invention is in no way limited to these examples.

Figure 3C:
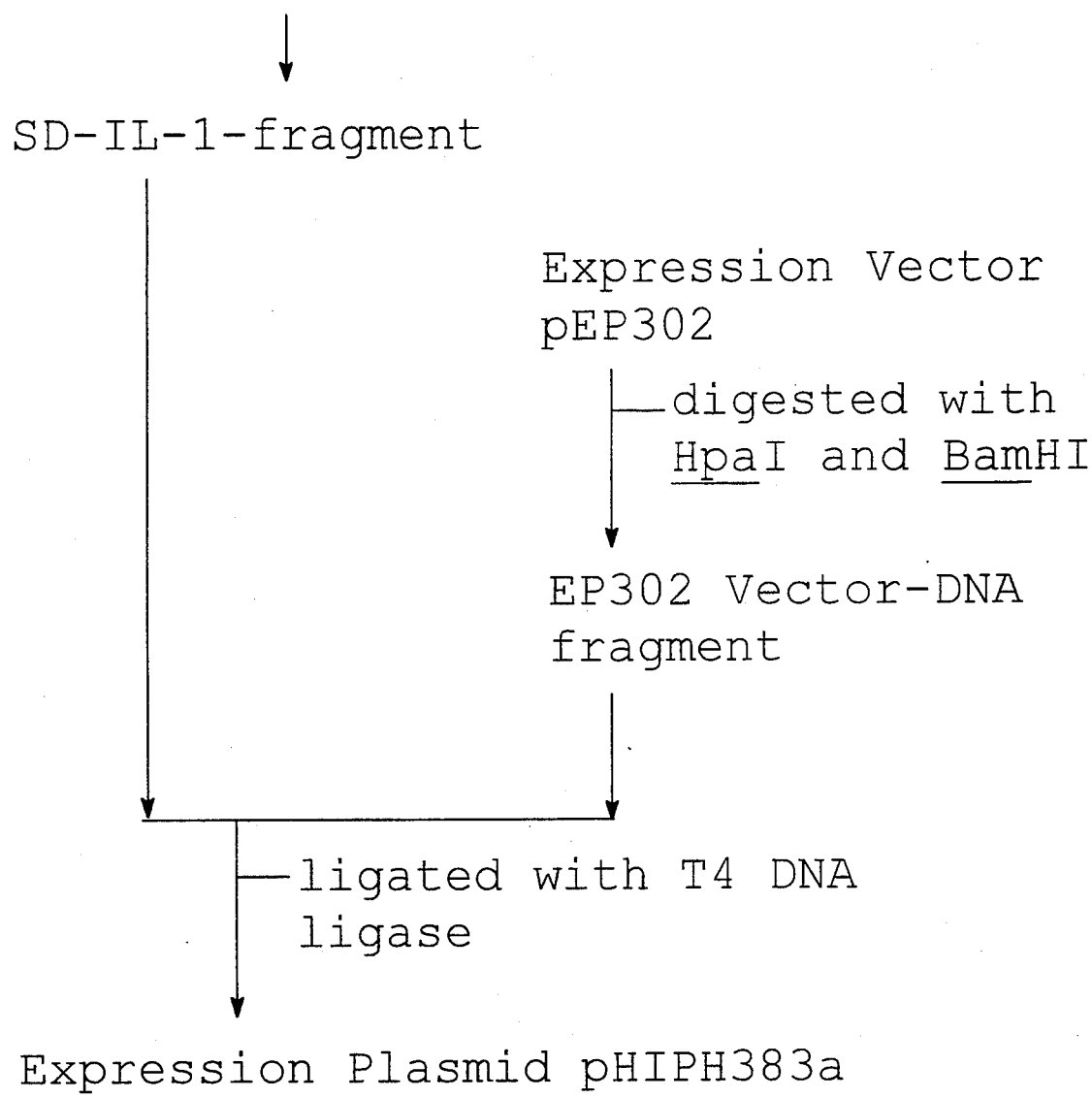

For a better understanding of the following Referential Examples, FIG. 1 to FIG. 3 are presented.

EXAMPLE 1

Production of human NCF polypeptide

Transformant cells for producing the human NCF polypeptide, *E. coli* HB101/pHNP101 obtained in Referential Example 2-(2) was cultivated in the LB broth [composition; 1% tryprone, 0.5% yeast extract, 1% sodium chloride (pH 7.5)], overnight at 37° C. The culture was inoculated in 100-fold volumes of the nutrient medium [composition 1.5% sodium phosphate, dibasic 12-water, 0.3% potassium phosphate, monobasic, 0.1% ammonium chloride, 2 mg/liter vitamin $B_1$, 0.5% casamino acids, 2 mM magnesium sulfate, 0.1 mM calcium chloride, 1% tryprone, 0.5% yeast extract, 1% sodium chloride and 0.4% glycerol] supplemented with 3-indoleacrylic acid at 2 μg/ml. The cultivation was done at 35° C. for 28 hours. The cells were collected by centrifugation, and suspended in 50 mM Tris-HCl buffer (pH 8.0) containing 0.2% lysozyme. The cell suspension was allowed to stand in ice water for 30 minutes.

Further, freezing in dry ice/ethanol and thawing at 37° C. were repeated to disrupt the cells. To the resulting cell homogenate, magnesium chloride and deoxyribonuclease I (Takers Shuzo Co., Ltd., Japan) were added at final concentrations of 1 mg and 2 U/ml, respectively. After incubating at 0° C. for 30 minutes, the insoluble pellet was collected by centrifugation and washed twice with 20 mg Tris-HCl buffer (pH 8.0) containing 0.75M urea and 1% Triton X-100. The washed pellet was dissolved with 6M guanidine hydrochloride in 5 mM phosphate buffer (pH 6.5). The clarified extract was obtained by centrifugation and dialyzed against 20 mM phosphate buffer (pH 6.5) (hereinafter referred to as PB). After centrifugation to remove the precipitate formed during the dimlysis, the dimlysate was applied onto a column of CM-Sepharose CL-6B (Pharmacia, Sweden) previously equilibrated with PB. The column was washed with PB, and eluted with a linear gradient of sodium chloride molarity from 0M to 0.5 g in PB. The fractions containing the human NCF polypeptide were collected and pooled, and concentrated by ultrafiltration. Further, the concentrate was subjected to gel filtration on Toyopearl HW-55 column (TOSOH Co., Japan) to obtain the highly purified human NCF polypeptide.

By SDS-polyacrylamide gel electrophoretic analysis, no impurity was detected in the highly purified human NCF polypeptide preparation.

EXAMPLE 2

Production of human NCF polypeptide

The highly purified NCF was obtained by dissolving the washed pellet from the transformant-homogenate as described in Example 1 with 8M urea in 5 mM phosphate buffer (pH 6.5), followed by using the same procedure as described in Example 1.

Referential Example 1

Cloning of cDNA encoding human NCF

The cDNA library was constructed by insertion of cDNA which was synthesized with a template polyadenylated mRNA obtained from normal human monocyte stimulated with lipopolysaccharide at 10 μg/ml for 6 hours, into the EcoRI site of the phage vector λ gt10. One half million individual plaques were screened for hybridization with [$^{32}$P]-labeled two kinds of chemically synthesized oligonucleotide probes represented by the following formulae, [C] and [D]:

and

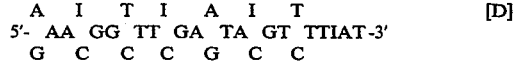

In the first screening, 13 putative positive clones were obtained. From these positive clones, one clone (termed r-MDNCF 2-1) was selected in the second screening by using another probe. The phage DNA in r-MDNCF 2-1 was subcloned into the pUC19 plasmid. The resulting recombinant plasmid was termed pUC19-1.7-5.

The cloned cDNA in a recombinant plasmid pU19-1.7-5 contains a nucleotide sequence encoding human NCF shown in Table 2.

Referential Example 2

Production of human NCF polypeptide

Human NCF polypeptide having an amino acid sequence represented by the formula [I] in Table 1, was produced by the following methods.

(1) Construction of an expression plasmid pHNP101

From the recombinant plasmid pUC19-1.7-5 in which human NCF cDNA was inserted as mentioned in Referential Example a, DNA fragment encoding the polypeptide corresponding to the amino acids from the 18th position to the 97th position from the N-terminus of human NCF precursor polypeptide (corresponding to the base sequence from the base No. 52 to No. 291 in Table 2) was isolated by digestion with restriction endonucleases PstI and EcoRI. This DNA fragment was then cloned into a phage vector M13mp18 (Takara Shuzo Co., Ltd., Japan) at a region between the restriction endonuclease cleavage site of PstI and that of EcoRI in the polylinker sequence. By using the resultant recombinant phage DNA, a specific base sequence being 5'-TTTAAATTATG-3' was inserted between the codon corresponding to Arg at the 27th position from the N-terminus of the human NCF precursor polypeptide and the codon corresponding to Set at the 28th position, by the technique of site-directed mutagenesis according to the method of Kunkel et al. (*Methods in Enzymol.*, 154, 367, 1987). The site-directed mutagenesis was carried out using a Muta-Gene in vitro mutagenesis kit according to the instruction manual (Bio-Rad Labs., USA). *E. coli* JM105 was infected with the recombinant phage DNA, and then it was cultivated to collect the recombinant phage. Then, *E. coli* CJ236 was infected with recombinant phage obtained as above and cultivated in 2xTY medium [composition; 1.6% tryprone, 1% yeast extract, 0.5% sodium chloride] supplemented with uridine and chloramphenicol at 1 µg/ml and 20 µg/ml, respectively, at 37° C. for 5 hours. The single-stranded phage DNA containing uracils was isolated from the culture medium.

Separately, mutagenic oligodeoxyribonucleotide primer consisting of 33 bases represented by the following formula [E] was chemically synthesized.

5'-GTTTTGCCAAGGTTTAAATTATGAGTG-CTAAAG-3'  [E]

The 5'-end of the mutagenic primer was previously phosphorylated. The phosophorylated primer was annealed with the single-stranded phage DNA containing uracils prepared as above in an annealing buffer [20 mM Tris-HCl buffer (pH 7.4) containing 2 mM magnesium chloride and 50 mM sodium chloride] by incubating at 70° C. for 10 minutes, followed by cooling down to 30° C. at a rate of 1° C. per minute. Then, the primer was extended with T4 DNA polymerase in a synthesis buffer [10 mM Tris-HCl buffer (pH 7.4) containing 0.4 mM each deoxynucleoside triphosphate (dGTP, dATP, dCTP, dTTP), 0.75 mM ATP, 3.75 mM magnesium chloride and 1.5 mM dithiothreitol] to synthesize a complementary strand and the ends were ligated with T4 DNA ligase by sequential incubating on ice for 5 minutes, at 25° C. for 5 minutes and at 37° C. for 90 minutes. The reaction was stopped by freezing at −20° C. The circular double-stranded DNA (heteroduplex) was introduced into *E. coli* JM105 cells, and they were cultivated to isolate the mutagenized double-stranded replicative form DNA. The nucleotide sequence of the mutagenized DNA was confirmed by sequencing the single-stranded BNA isolated from the culture medium.

The resultant mutagenized double-stranded DNA was digested with restriction endonucleases DraI and EcoRI in order to isolate a DNA fragment containing most of the coding region for human NCF polypeptide. The isolated DNA fragment is, hereinafter, referred to as the NCF (DraI-EcoRI)-fragment.

This NCF (DraI-EcoRI)-fragment was ligated by T4 DNA ligase with a chemically synthesized oligodeoxynucleotide adaptor represented by the following formula [F].

5'-AATTCATGATGAC  [F]
3'-GTACTACTGAGCT

The resultant ligated DNA fragment is referred to as NCF (DraI-XhoI)-fragment.

Separately, an expression plasmid pEP205 as mentioned in Referential Example 3 was digested with restriction endonucleases DraI and XhoI, and the resulting target DNA fragment including an ampicillin-resistance gene and a replication origin (hereinafter referred to as the EP205 vector-DNA fragment) was isolated, and this EP205 vector-DNA fragment was ligated by T4 DNA ligase with the NCF (DraI-XhoI)-fragment previously prepared in order to construct an expression plasmid pHNP101 for producing human NCF (see FIG. 1).

(2) Transformation of *Escherichia coli*

The resulting expression plasmid pHNP101 was introduced into *E. coli* HB101 by the following manner.

*E. coli* HB101 was inoculated in the LB broth [composition; 1% tryprone, 0.5% yeast extract, 1% sodium chloride (pH 7.5)], and cultivated overnight at 30° C. One milliliter of the resulting culture was inoculated in 100 ml of LB broth and further cultivated at 30° C. until the turbidity at 600 nm of the culture reached approximately 0.6. After standing for 30 minutes in ice water, the cells were collected by centrifugation. They were resuspended in 50 ml of 50 mM calcium chloride, and allowed to stand for 60 minutes in ice water. Then, the cells were collected by centrifugation and again suspended in 10 ml of 50 mM calcium chloride containing 20% glycerol.

To this cell suspension, the expression plasmid pHNP101 was mixed and incubated sequentially in ice water for 20 minutes and at room temperature for 60 minutes. Then, the LB broth was added to the cell suspension, and it was cultivated under shaking at 37° C. for 60 minutes. An aliquot of the resulting cell suspension was seeded on the LB agar (1.5% agar) plates containing ampicillin at 25 µg/ml. After cultivation at 37° C. overnight, ampicillin-resistant colonies were selected to obtain transformants. One of the transformants was named *E. coli* HB101/pHNP101 and it was used for production of the human NCF polypeptide. (3) Production of human NCF polypeptide

*E.coli* HB101/pHNP101 obtained as above was cultivated in the LB broth overnight at 37° C. The culture was inoculated in 100-fold volumes of the nutrient medium mentioned in Example 1 supplemented with 3-indoleacrylic acid at 20 µg/ml. The cultivation was done at 35° C. for 28 hours. The cells were collected by centrifugation, and suspended in 50 mM Tris-HCl buffer (pH 8.0) containing 0.1% lysozyme and 30 mM sodium chloride. The suspension was allowed to stand in ice water for 30 minutes. Further, freezing in a dry ice/ethanol bath and thawing at 37° C. were repeated to disrupt the cells. After adding 1/50 volume of 10% ethyleneimine polymer, a clarified cell-extract was obtained by centrifugation. To this cell-extract, ammonium sulfate was added to give a 70% saturation, and the formed precipitate was collected by centrifugation. The precipitate was dissolved in distilled water and it was dialyzed against 5 mM phosphate buffered saline (pH 6.5). The dialysate was applied onto a column of Sephacryl S-200, and the fractions containing polypeptides having about 6 to 10 kD were collected and pooled. The molecular sizes of polypeptides in each eluate were measured by SDS-polyacrylamide gel electrophoretic analysis. The pooled fraction was dialyzed against PB mentioned in Example 1. Then, the dialysate was applied onto a column of CM-Sepharose CL-6B previously equilibrated with PB. The column was washed with PB, and eluted with a linear gradient of sodium chloride molarity from 0M to 0.5M in PB. The fractions containing the human NCF polypeptide were collected and pooled, and concentrated by ultra-filtration. Further, the concentrate was subjected to gel filtration on Toyopearl HW-55 column to obtain the highly purified human NCF polypeptide.

Referential Example 3

Construction of an expression vector pHP205

Plasmid pBR322 was digested with restriction endonucleases AvaI and PvuII, and the resulting larger DNA fragment (about 3.7 kbp in size) was isolated. After filling-in its cohesive ends to blunt-ends with E. coli DNA polymerase I (Klenow fragment) in the presence of dGTP, dATP, dCTP and dTTP, both ends were ligated by T4 DNA ligase to construct a new plasmid vector (designated pBRS6), which was deleted a copy number regulatory gene region located near the replication origin of the plasmid pBR322.

The plasmid vector pBRS6 was digested with restriction endonucleases EcoRI and PstI, and a smaller DNA fragment containing an upstream region of the ampicilin-resistance gene (about 0.75 kbp in size) was isolated. The resultant DNA fragment is referred to as the Amp (PstI-EcoRI)-fragment.

This Amp (PstI-EcoRI)-fragment was cloned in a phage vector M13mp18 as mentioned in Example. By using the resultant recombinant phage DNA, one base (T) in the nucleotide sequence of the Amp (PstI-EcoRI)-fragment was changed to another base (C) by the site-directed mutagenesis according to the method as mentioned in Referential Example 2, in order to eliminate the specific nucleotide sequence (AAATTT) recognizable with the restriction endonuclease DraI.

The single-stranded phage DNA containing uracils was isolated from the culture medium of E. coli CJ236 infected with the above recombinant phage DNA. As a mutagenic primer, the oligodeoxyribonucleotide represented by the following formula [G] was chemically synthesized.

ti 5'-CAGAACTTTGAAAGTGCTC-3'  [G]

The phosphorylated primer was annealed with the uracil-containing DNA template. According to the method described in Referential Example 2, the desired mutagenized double-stranded DNA was isolated.

The resultant mutagenized double-stranded DNA was digested with restriction endonucleases PstI and EcoRI in order to isolate a DNA fragment corresponding to the Amp (PstI-EcoRI)-fragment as mentioned above, but not containing the restriction endonuclease DraI cleavage recognition sequence [hereinafter referred to as the mutated Amp (PstI-EcoRI)-fragment]. The mutated Amp (PstI-EcoRI)-fragment was ligated with the larger DNA fragment isolated from the vector pBRS6 by digestion with restriction endonucleases EcoRI and PstI, in order to construct a new vector which was eliminated the DraI cleavage recognition sequence in the ampicillin resistance gene of the plasmid vector pBRS6. This new vector is designated pBRS601.

Further, this new vector pBRS601 was digested with restriction endonuclease DraI, and the resulting larger DNA fragment was ligated with SmaI linker (Takara Shuzo Co., Ltd., Japan) by T4 DNA ligase to construct a new plasmid vector. This resulting new plasmid vector is a derivative of plasmid pBRS6 and is not containing any recognition sequences for the restriction endonuclease DraI. This new plasmid vector is designated pBRS602.

The nucleotide sequence of the SmaI linker is shown below.

5'-CCCGGG-3'

Further, this new vector pBRS602 was digested with restriction endonuclease AatII and SalI, and the resulting larger DNA fragment was isolated [hereinafter referred to as the pBRS602 (AatII-SalI)-fragment].

Separately, an expression plasmid pHIPH383a for producing human interleukin-1α as mentioned in Referential Example 4, was digested with restriction endonucleases AatII and SalI, and resulting DNA fragment containing E. coli tryptophan promoter sequence and coding region for human interleukin-1α was isolated. This resulting DNA fragment is referred to as the trp promoter/IL-1α-DNA fragment.

This trp promoter/IL-1α-DNA fragment was ligated with the pBRS602 (AatII-SalI)-fragment by T4 DNA ligase to construct a new expression plasmid (see FIG. 2).

This new expression plasmid is designated pEP205.

Referential Example 4

Construction of an expression plasmid pHIPH383a

The cloned cDNA encoding human interleukin-1α precursor polypeptide was isolated according to the method described in European Patent Publication No. 0188920.

From the recombinant plasmid pHL4 containing human interleukin-1α precursor cDNA (Furutani, Y., et al., Nucleic Acids Res., 13, 5869, 1985), the cDNA insert was isolated by digestion with restriction endonuclease PstI, and further digested with restriction endonucleases EcoRI and BstNI, to isolate a DNA fragment (411 bp in size) containing a middle portion of the coding region for the mature human interleukin-1α. The isolated DNA fragment corresponds to the nucleotide sequence from base No. 398 to No. 808 in Table 5 shown in European Patent Publication No. 0188920.

This DNA fragment was sequentially ligated by T4 DNA ligase with chemically synthesized oligodeoxyribonucleotide adaptors represented by the following formulae [H] and [J]. The resulting DNA fragment is referred to as the SD-IL-1-fragment.

The synthetic oligodeoxyribonucleotide adaptor [H] was prepared by sequential ligation of the following five kinds of DNA fragments represented by formula [a]~[e].

```
5'-AACTAGTACGCAAGTTCAC            [a]
3'-TTGATCATGCGTTCAAGTGCATT
```

```
5'-GTAAAAGGAGGTTTAAA              [b]
3'-TTCCTCCAAATTTAATAC
```

```
5'-TTATGTCATCACCTTTTAG            [c]
3'-AGTAGTGGAAAATCGAAGG
```

-continued

```
5'-CTTCCTGAGCAATGTGAAATACAACTTTA    [d]
3'-ACTCGTTACACTTTATGTTGAAATACTC
``` and

```
5'-TGAGGATCATCAAATACG    [e]
3'-CTAGTAGTTTATGCTTAA
```

A base sequence of the formula [J] was as follows;

```
5'-AGGCGTGATGACTCGA    [J]
3'-CCGCACTACTGAGCTCTAG
```

Separately, an expression vector pEP302 (Furutani, Y., et al., *Nucleic Acids Res.*, 13, 5869, 1985) was digested with restriction endonucleases HpaI and BamHI, and the resulting larger DNA fragment containing *E. coli* tryptophan promoter sequence and an ampicillin resistance gene, was isolated (hereinafter referred to as the EP302 vector-DNA fragment).

The EP302 vector-DNA fragment was ligated by T4 DNA ligase with SD-IL-1-fragment prepared as above to construct an expression plasmid pHIPH383a for producing the mature human interleukin-1α polypeptide (see FIG. 3).

TABLE 1

SerAlaLysGluLeuArgCysGlnCysIleLysThr
TyrSerLysProPheHisProLysPheIleLysGlu
LeuArgValIleGluSerGlyProHisCysAlaAsn
ThrGluIleIleValLysLeuSerAspGlyArgGlu
LeuCysLeuAspProLysGluAsnTrpValGlnArg
ValValGluLysPheLeuLysArgAlaGluAsnSer
formula [I]

TABLE 2

Nucleotide Sequence of Human NCF Precursor cDNA and Its Deduced Amino Acid Sequence

| | | |
|---|---|---|
| MetThrSerLysLeu | AlaValAlaLeuLeu | 10 |
| ATGACTTCCAAGCTG | GCCGTGGCTCTCTTG | 30 |
| AlaAlaPheLeuIle | SerAlaAlaLeuCys | 20 |
| GCAGCCTTCCTGATT | TCTGCAGCTCTGTGT | 60 |
| GluGlyAlaValLeu | ProArgSerAlaLys | 30 |
| GAAGGTGCAGTTTTG | CCAAGGAGTGCTAAA | 90 |
| GluLeuArgCysGln | CysIleLysThrTyr | 40 |
| GAACTTAGATGTCAG | TGCATAAAGACATAC | 120 |
| SerLysProPheHis | ProLysPheIleLys | 50 |
| TCCAAACCTTTCCAC | CCCAAATTTATCAAA | 150 |
| GluLeuArgValIle | GluSerGlyProHis | 60 |
| GAACTGAGAGTGATT | GAGAGTGGACCACAC | 180 |
| CysAlaAsnThrGlu | IleIleValLysLeu | 70 |
| TGCGCCAACACAGAA | ATTATTGTAAAGCTT | 210 |
| SerAspGlyArgGlu | LeuCysLeuAspPro | 80 |
| TCTGATGGAAGAGAG | CTCTGTCTGGACCCC | 240 |
| LysGluAsnTrpVal | GlnArgValValGlu | 90 |
| AAGGAAAACTGGGTG | CAGAGGGTTGTGGAG | 270 |
| LysPheLeuLysArg | AlaGluAsnSer | 99 |
| AAGTTTTTGAAGAGG | GCTGAGAATTCA | 297 |

What is claimed is:

1. A method for preparing by direct expression an active recombinant human neutrophil chemotactic factor polypeptide consisting of an amino acid sequence of the formula SerAlaLysGluLeuArgCysGlnCysIleLysThr TyrSerLysProPheHisProLysPheIleLysGlu LeuArgValIleGluSerGlyProHisCysAlaAsn ThrGluIleIleValLysLeuSerAspGlyArgGlu LeuCysLeuAspProLysGluAsnTrpValGlnArg ValValGluLysPheLeuLysArgAlaGluAsnSer which comprises:
cultivating *Escherichia coli* cells harboring an expression vector inclusive of a base sequence encoding said polypeptide;
disrupting said cells to form a transformant-homogenate;
collecting a precipitate from the transformant-homogenate; and
treating the precipitate with urea or guanidine hydrochloride at a concentration sufficient to solubilize said polypeptide.

2. The method for preparing human neutrophil chemotactic factor polypeptide according to claim 1, wherein said concentration of urea or guanidine hydrochloride is more than 4M.

3. The method for preparing human neutrophil chemotactic factor polypeptide according to claim 1, wherein said concentration of urea or guanidine hydrochloride is 6M to 10M.

4. The method for preparing human neutrophil chemotactic factor polypeptide according to claim 1, wherein said concentration of urea or guanidine hydrochloride is 4M to 10M.

5. The method for preparing human neutrophil chemotactic factor polypeptide according to claim 1, wherein guanidine hydrochloride is used to solubilize said polypeptide.

6. The method for preparing human neutrophil chemotactic factor polypeptide according to claim 1, wherein urea is used to solubilize said polypeptide.

7. The method for preparing human neutrophil chemotactic factor polypeptide according to claim 1, which further comprises the steps of removing said urea or guanidine hydrochloride.

8. The method for preparing human neutrophil chemotactic factor polypeptide according to claim 7, wherein said urea or guanidine hydrochloride is removed by dialysis to obtain said solubilized polypeptide.

9. The process of claim 8, wherein said polypeptide is further purified to obtain a highly purified polypeptide in which impurity cannot be detected by SDS-polyacrylamide gel electrophoretic analysis.

10. The process of claim 1, wherein the transformant-homogenate is treated with deoxyribonuclease to breakdown nucleic acids.

* * * * *